United States Patent
Loef et al.

(10) Patent No.: US 8,824,624 B2
(45) Date of Patent: Sep. 2, 2014

(54) CONTACTLESS POWER CHAIN

(75) Inventors: Christoph Loef, Aachen (DE); Peter Luerkens, Aachen (DE); Hendrikus Wilhelmus Leonardus Antonius Maria Van Lierop, Weert (NL); Joseph Gertrudis Leonardus Otten, Maria-Hoop (NL)

(73) Assignee: Koninklijke Philips N.V., Eindhoven (NL)

( * ) Notice: Subject to any disclaimer, the term of this patent is extended or adjusted under 35 U.S.C. 154(b) by 231 days.

(21) Appl. No.: 13/321,198

(22) PCT Filed: May 4, 2010

(86) PCT No.: PCT/IB2010/051960
§ 371 (c)(1),
(2), (4) Date: Nov. 18, 2011

(87) PCT Pub. No.: WO2010/143084
PCT Pub. Date: Dec. 16, 2010

(65) Prior Publication Data
US 2012/0069955 A1      Mar. 22, 2012

Related U.S. Application Data

(60) Provisional application No. 61/186,022, filed on Jun. 11, 2009.

(51) Int. Cl.
*H05G 1/10* (2006.01)
*A61B 6/00* (2006.01)
*H01F 38/18* (2006.01)

(52) U.S. Cl.
CPC .. *H05G 1/10* (2013.01); *A61B 6/56* (2013.01); *H01F 38/18* (2013.01)
USPC ............................................ 378/15; 378/204

(58) Field of Classification Search
CPC ....................................................... H01F 38/18
USPC ............................................................ 378/15
See application file for complete search history.

(56) References Cited

U.S. PATENT DOCUMENTS

| 4,396,797 A | 8/1983 | Sakuragi et al. |
| 5,609,771 A | 3/1997 | Pelmulder |

(Continued)

FOREIGN PATENT DOCUMENTS

| DE | 2234472 | 1/1974 |
| DE | 102006044704 A1 | 3/2008 |

(Continued)

*Primary Examiner* — Hoon Song
*Assistant Examiner* — Dani Fox

(57) ABSTRACT

An imaging system (100) includes a stationary gantry (102) and a rotating gantry (104). The rotating gantry (104) includes a first component (110, 114, 116) supplied with first power and a second component supplied with second power, wherein the first and second power are different. A contactless power chain (118) includes a first transformer (202, 204, 306) for transferring the first power from the stationary gantry (102) to the rotating gantry (104) and a second transformer (202, 204, 306) for transferring the second power from the stationary gantry (102) to the rotating gantry (104). The first and second transformers (202, 204, 306) are shifted relative to each other along the longitudinal axis (108) by a pre-determined finite non-zero distance (240). In another embodiment, an imaging system (100) includes a stationary gantry (102) and a rotating gantry (104) that rotates about a longitudinal axis (108). A contactless power chain (118) transfers power from the stationary gantry (102) to the rotating gantry (104), wherein windings (214, 218, 230, 234) of the contactless power chain (118) are carried by a non-resin based carrier (700).

29 Claims, 9 Drawing Sheets

(56) References Cited

U.S. PATENT DOCUMENTS

| | | |
|---|---|---|
| 7,197,113 B1 * | 3/2007 | Katcha et al. ............... 378/101 |
| 7,402,934 B1 | 7/2008 | Gabrys |
| 7,957,786 B2 | 6/2011 | Katcha et al. |
| 2002/0070623 A1 * | 6/2002 | Rehder et al. ............... 310/232 |
| 2005/0226380 A1 | 10/2005 | Katcha et al. |
| 2009/0116618 A1 * | 5/2009 | Nakayama et al. ........... 378/107 |

FOREIGN PATENT DOCUMENTS

| | | |
|---|---|---|
| EP | 0474298 A1 | 3/1992 |
| EP | 1408310 A1 | 4/2004 |
| JP | 2002252129 A | 9/2002 |
| WO | 2008094919 A2 | 8/2008 |
| WO | 2009147550 A1 | 12/2009 |

\* cited by examiner

CONTACTLESS POWER CHAIN

CROSS REFERENCE TO RELATED APPLICATIONS

This application claims the benefit of U.S. provisional application Ser. No. 61/186,022 filed Jun. 11, 2009, which is incorporated herein by reference.

The following generally relates to a contactless power chain, and is described with particular application to computed tomography (CT); however, it is also amenable to other imaging and non-imaging modalities.

A computed tomography (CT) scanner generally includes a stationary gantry and a rotating gantry rotatably supported by the stationary gantry. The rotating gantry supports components such as an x-ray tube, a detection system and auxiliary components. The x-ray tube emits radiation that traverses an examination region (and any subject or object disposed therein), and the detection system detects the radiation. The rotating gantry is configured to alternatively remain stationary or rotate around the examination region for scanning.

The x-ray tube, as well as some of the other components supported by the rotating gantry, requires power for operation. Conventionally, power for both the x-ray tube and the other components is transferred from the stationary gantry to the rotating gantry over a slip-ring. Unfortunately, slip-ring technology is not well suited for the higher power demands of higher power scanners. In addition, slip-ring brushes are susceptible to wear, which may decrease reliability.

The literature has proposed the use of contactless transformers to transfer power from the stationary to the rotating gantry. With contactless transformers, a first transformer would transfer higher power for the x-ray tube, and a second transformer would transfer relatively lower power for the other components. The primary windings of the transformers would be mounted on the stationary gantry and the secondary windings of the transformers would be mounted on the rotating gantry. The transformers would be arranged on the stationary and rotating gantries in the form of concentric rings.

Unfortunately, leakage flux from a transformer may induce a field in the other transformer. This may lead to coupling of the transformers. As a consequence, the first transformer may induce a voltage in the windings of second transformer, and/or the second transformer may induce a voltage in the windings of the first transformer. In addition, conventional techniques for mounting the wires in the transformers may lead to windings that are not properly aligned and/or insulated.

Aspects of the present application address the above-referenced matters and others.

According to one aspect, an imaging system includes a stationary gantry and a rotating gantry that rotates about a longitudinal axis. The rotating gantry includes a first component supplied with first power and a second component supplied with second power, wherein the first and second power are different. A contactless power chain includes a first transformer for transferring the first power from the stationary gantry to the rotating gantry and a second transformer for transferring the second power from the stationary gantry to the rotating gantry. The first and second transformers are shifted relative to each other along the longitudinal axis by a pre-determined finite non-zero distance.

In another embodiment, an imaging system includes a stationary gantry, a rotating gantry that rotates about a longitudinal axis, and a contactless power chain that transfers power from the stationary gantry to the rotating gantry. Windings of the contactless power chain are carried by a non-resin based carrier.

In another embodiment, a method includes transferring first and second different power from a stationary gantry to a rotating gantry of an imaging system and scanning an object or subject with the imaging system. The imaging system includes at least two transformers for respectively transferring the first and second power. The at least two transformers are shifted relative to each other along a longitudinal axis by a finite non-zero distance.

In another embodiment, a method includes transferring power from a stationary gantry to a rotating gantry of an imaging system and scanning an object or subject with the imaging system. The imaging system includes at least one transformer for transferring the power. The windings of at least one of the transformers are supported therein by a non-resin based carrier.

The invention may take form in various components and arrangements of components, and in various steps and arrangements of steps. The drawings are only for purposes of illustrating the preferred embodiments and are not to be construed as limiting the invention.

Figure 1:
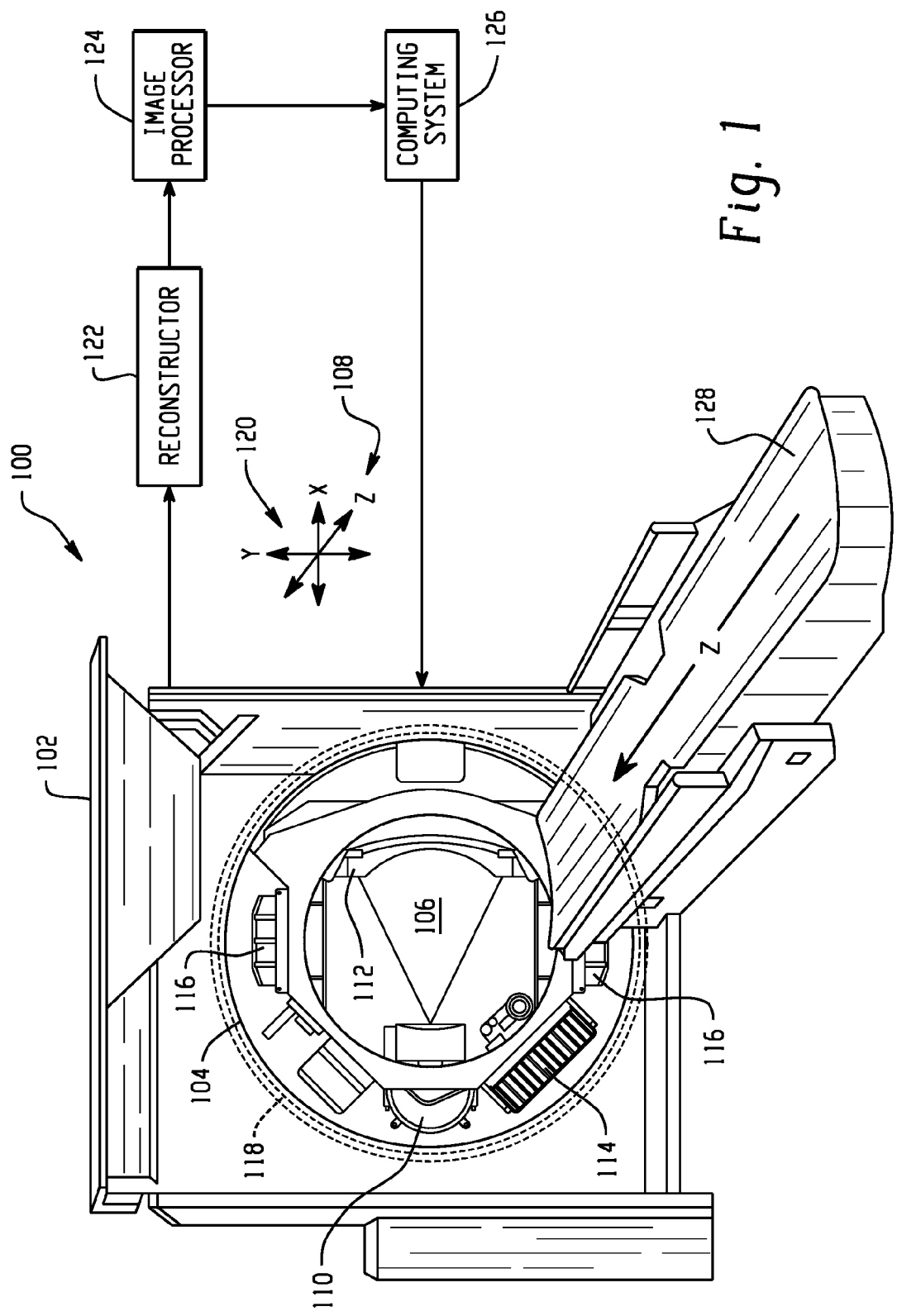
FIG. 1 illustrates an imaging system and contactless power chain.

FIG. 1 illustrates an imaging system 100 such as a CT scanner. The imaging system 100 includes a stationary gantry 102 and a rotating gantry 104. The rotating gantry 104 is rotatably supported by the stationary gantry 102 via a bearing (not visible). The rotating gantry 104 is configured to alternatively remain stationary or rotate around an examination region 106 about a longitudinal axis 108 (z-axis) when scanning a subject or object disposed in the examination region 106.

The rotating gantry 104 supports a radiation source 110, such as an x-ray tube that emits radiation, and a radiation sensitive detector array 112, which detects radiation traversing the examination region 106 and generates a signal indicative thereof. The radiation sensitive detector array 112 subtends an angular arc opposite the radiation source 110 across the examination region 106. The illustrated rotating gantry 104 also supports a heat exchanger 114, a power module 116, and/or one or more other components requiring power for operation, as well as one or more components that do not require power.

A contactless power chain 118 is arranged with respect to the stationary and rotating gantries 102 and 104 and transfers power from the stationary gantry 102 to the rotating gantry 104 for powering components supported by the rotating gantry 104. As described in greater detail below, in one embodiment the power chain 118 includes at least two transformers that are radially offset from each other along a transverse axis 120 (x/y direction) and shifted with respect to each other along the z-axis 108. In one instance, this allows for reducing coupling (e.g., from leakage current, etc.) relative to a configuration in which the at least two transformers are not shifted from each other along the z-axis 108. Also described in greater detail below, in one instance the winding of a transformer are packaged using a packing apparatus, which allows for maintaining the winding substantially in a predetermined alignment and insulation.

A reconstructor 122 reconstructs projection data generated by the detector array 112 and generates volumetric data indicative of the scanned object or subject. An image processor 124 processes the volumetric image data generated by the reconstructor 122 and generates one or more images indicative of the scanned object or subject.

A general purpose computing system 126 serves as an operator console. The computing system 126 includes human readable output devices such as a display and/or printer and input devices such as a keyboard and/or mouse. Software resident on the computing system 126 allows the operator to control the operation of the system 100.

A patient support 128, such as a couch, supports a patient in the examination region 106. The patient support 128 is movable along the z-axis 108 in coordination with the rotation of the rotating gantry 104 to facilitate helical, axial, or other desired scanning trajectories.

Figure 2:
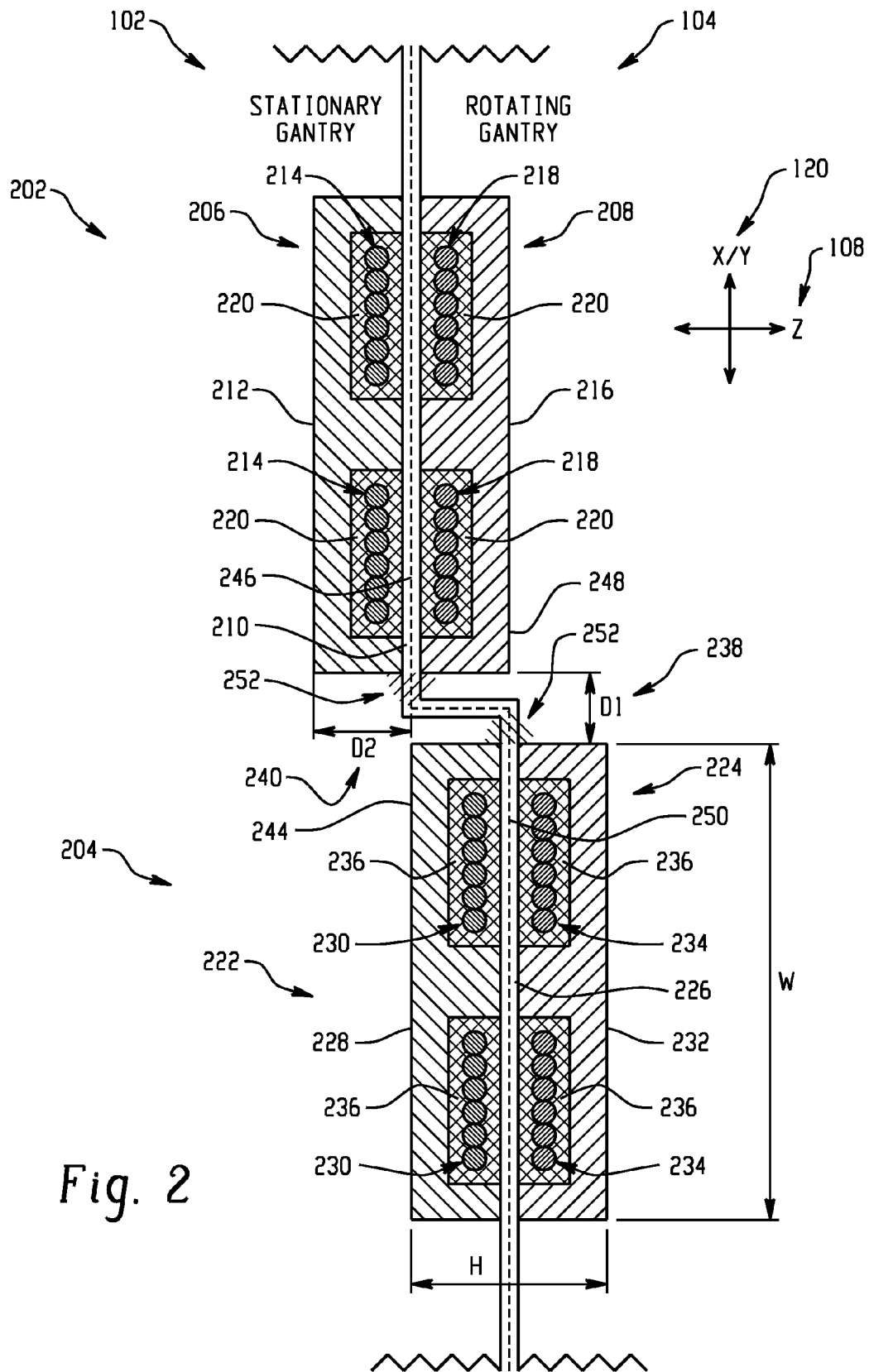
FIGS. 2, 5 and 6 illustrate a dual transformer contactless power chain.

FIG. 2 illustrates a cross-sectional view of an exampled embodiment of the contactless power chain 118. The illustrated contactless power chain 118 includes at least two transformers 202 and 204. In other embodiments, the contactless power chain 118 may include one or more than two transformers. In this example, the transformers 202 and 204 have a similar height (H) and a similar width (W). In other embodiments, the height (H) and/or width (W) can be different. In addition, the shapes of the transformers 202 and 204 can be similar (as illustrated) or different.

One of the transformers 202 or 204 is configured to transfer first power from the stationary gantry 102 to the rotating gantry 104 and the other of the transformers 202 or 204 is configured to transfer second different power from the stationary gantry 102 to the rotating gantry 104. In one instance, one of the first or second power is for powering the radiation source 110 and/or other higher power components, and the other of the first or second power is used for powering the lower power components. Example power ranges include, but are not limited to, one hundred (100) to two hundred (200) kilowatts (kW) such as one hundred and fifty (150) kW for higher power components, and one (1) to fifteen (15) kW such as five (5) kW for lower power components.

The transformer 202 includes a primary side 206, which is affixed to the stationary gantry 102, and a secondary side 208, which is affixed to the rotating gantry 104. The primary and secondary sides 206 and 208 are separated by an air gap 210. The primary side 206 includes a primary side core 212 and primary windings 214, and the secondary side 208 includes a secondary side core 216 and secondary windings 218. In this embodiment, the primary and secondary windings 214 and 218 are respectively aligned and insulated in the cores 212 and 216 via an insulator 220 such as a resin, insulation packaging (as described below), or otherwise.

Similarly, the transformer 204 includes a primary side 222, which is affixed to the stationary gantry 102, and a second side 224, which is affixed to the rotating gantry 104. The primary and secondary sides 222 and 224 are separated by an air gap 226. The primary side 222 includes a primary side core 228 and primary windings 230, and the secondary side 224 includes a secondary side core 232 and secondary windings 234. Likewise, the primary and secondary windings 230 and 234 are respectively aligned and insulated in the cores 228 and 232 via an insulator 236.

The transformers 202 and 204 are arranged, with respect to each other offset along the transverse (x/y) direction 120 by a finite distance (D1) 238. The transformers 202 and 204 are also arranged, with respect to each other, shifted along the longitudinal (z) direction 108 by a finite distance (D2) 240. The illustrated transformers 202 and 204 are shifted along the longitudinal direction 108 so that a bottom 244 of the core 228 of the primary side 222 of the transformer 204 is in substantial alignment with a center 246 of the gap 210 between the primary and secondary sides 206 and 208 of the transformer 202. Likewise, a bottom 248 of the core 216 of the secondary side 208 of the transformer 202 is in substantial alignment with a center 250 of the gap 226 between the primary and secondary sides 222 and 224 of the transformer 204. In other embodiments, the distance (D2) 240 is less or greater than the illustrated distance.

During operation, leakage fields 252 of the transformers 202 and 204 can induce magnetic flux into each other. This induced coupling may lead to cross-talk, which may result in an additional voltage being induced in the windings 214, 218, 230 and 234. Generally, the amount of the induced voltage depends at least on the distance between the air gaps 210 and 226 of the respective transformers 202 and 204. Arranging the transformers 202 and 204, with respect to each other, with the illustrated shift (D2) 240 increases the distance between the air gaps 210 and 226 relative to an arrangement in which the transformers 202 and 204 are not offset (e.g., D2=0).

Hence, the illustrated arrangement allows for reducing cross-talk between the transformers 202 and 204 and thus the amount of induced voltage (and flux) relative to an arrangement in which the transformers 202 and 204 are not shifted (e.g., D2=0). Further, arranging the transformers 202 and 204 such that their air gaps 210 and 226 overlap the cores 228 and 216 may lead to short circuiting the leakage flux through the cores 228 and 216, which may further reduce coupling. In addition, arranging the transformers 202 and 204 as such may also reduce the footprint relative to a configuration in which at least one of the transformers 202 and 204 is rotated along the z-axis 108.

Figure 3:
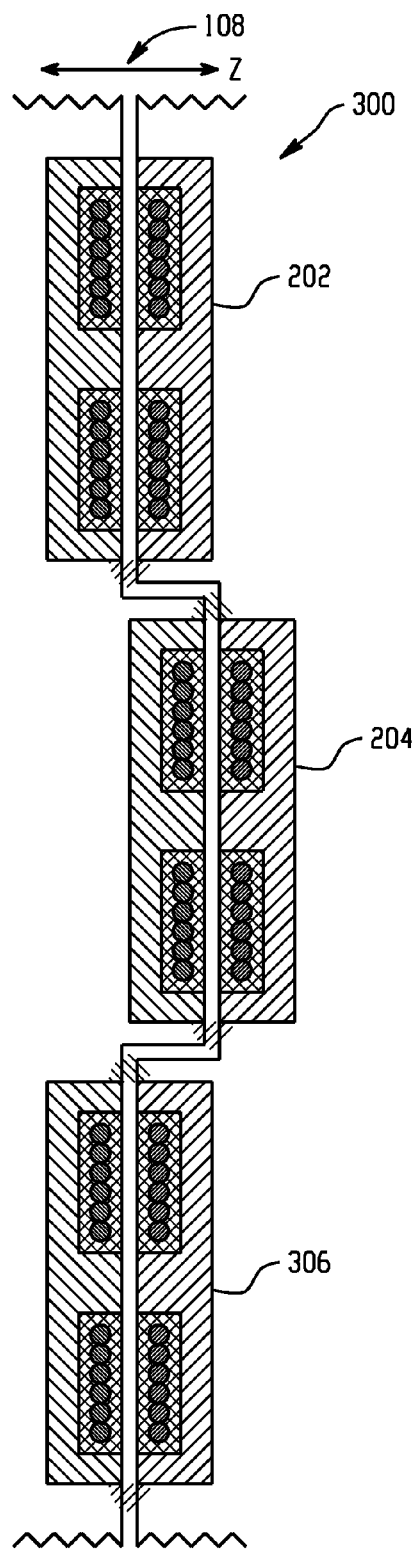
FIGS. 3 and 4 illustrate an N transformer contactless power chain.
Figure 4:
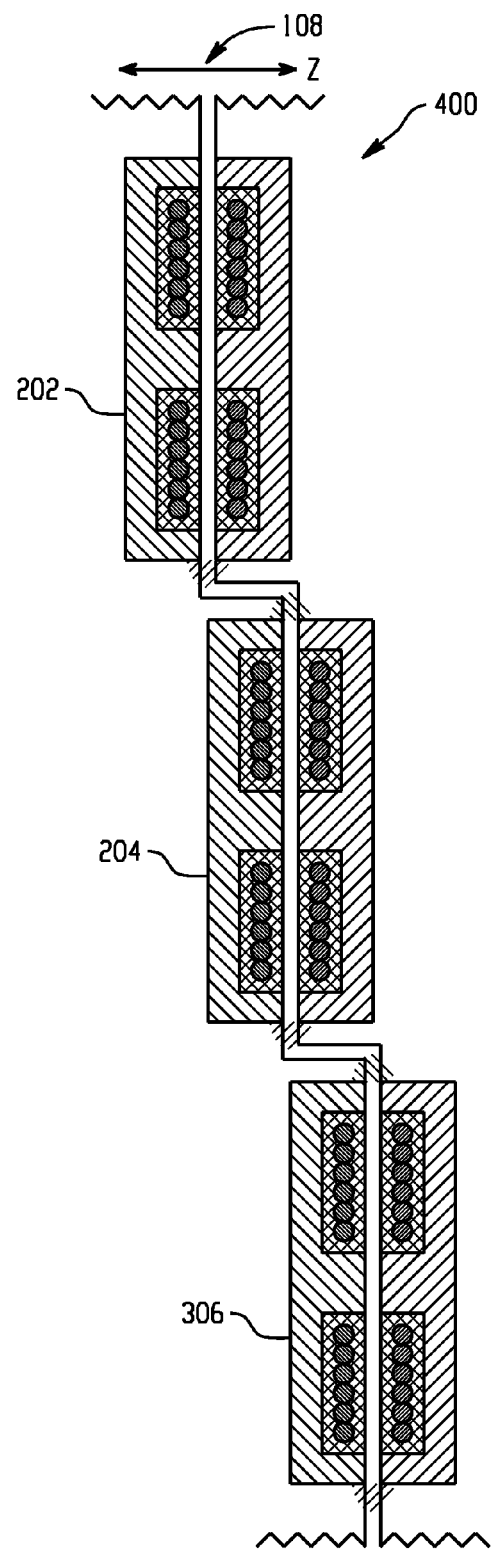

FIGS. 3 and 4 illustrate example embodiments 300 and 400 in which the contactless power chain 118 respectively includes more than two transformers such as transformers 202, 204 and 306. Other embodiments may include more or less transformers. As shown, in FIG. 3, the direction of the shift alternates along the z-axis 108. In FIG. 4, each successive transformer is shifted in the same direction along the z-axis 108.

Figure 5:
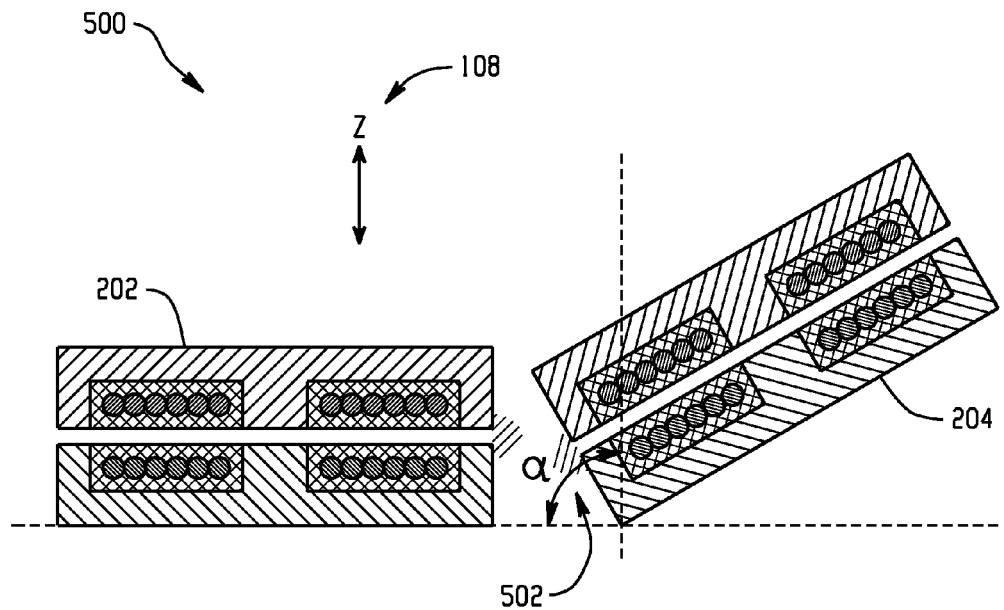
Figure 6:
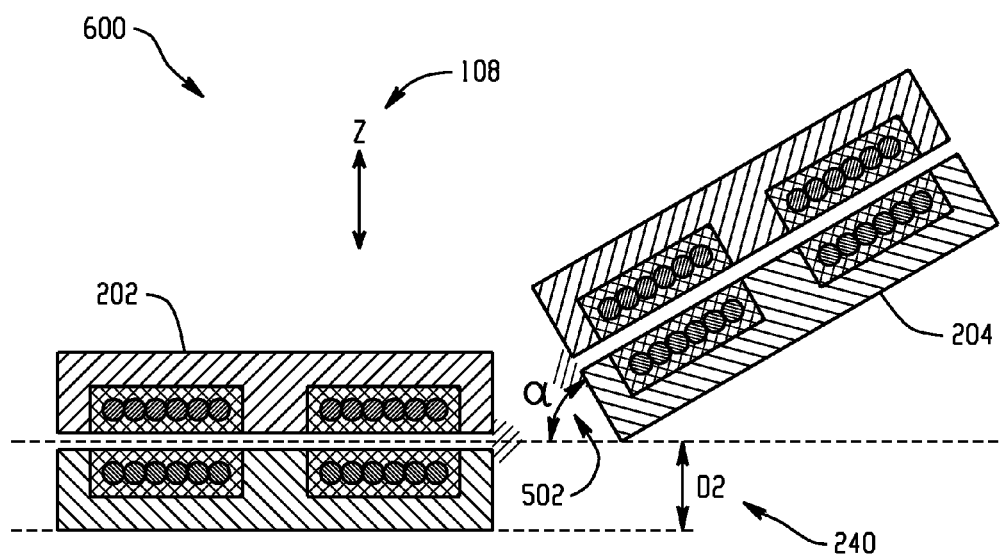

FIGS. 5 and 6 respectively illustrate embodiments 500 and 600 in which at least one of the transformers 202 and 204 is pivoted about the z-axis 108. In FIG. 5, the transformer 204 is pivoted by an angle α 502 with respect to the z-axis direction 108. In FIG. 6, the transformers 204 is shifted by D2 240 and pivoted by the angle α 502. In one instance, the angle α 502 is in a range between zero (0) and one hundred and forty-five (145) degrees such as ninety (90) degrees. Other arrangements are also contemplated herein.

In another embodiment, if the operation frequency of the current in the transformers 202 and 204 is different, filters can be used to further reduce cross-talk. Such filters may be located at the winding terminals or otherwise.

As noted in connection with FIG. 2, the transformer windings can be held in alignment and insulated via the insulator 220, 236. In FIG. 2, the insulator 220, 236 includes a resin. In FIGS. 7, 8, 9 and 10, the insulator includes a carrier that inserts into a core of a transformer.

Figure 7:
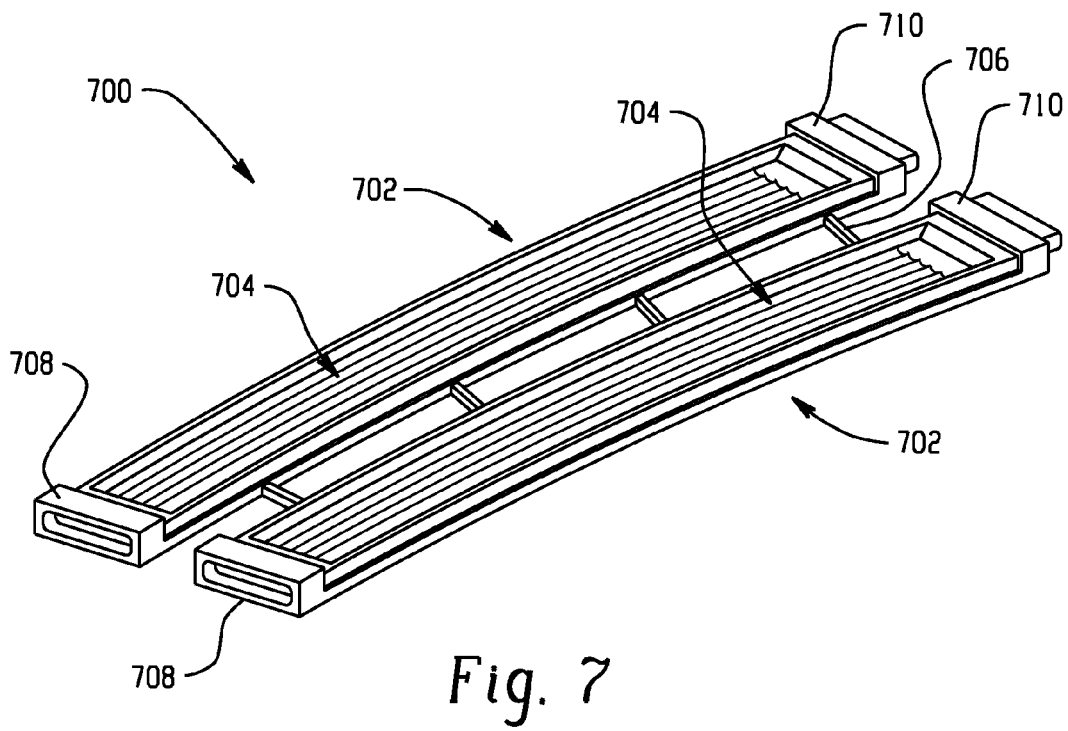
FIGS. 7, 8 and 9 illustrate an example carrier for a transformer.

Initially referring to FIG. 7, a carrier 700 includes an elongate channel 702 having at least one open side 704 and closed sides. The illustrated channel 702 includes three closed sides, and is U-shaped with concentric grooves at the bottom, which can be used to facilitate pre-aligning the windings. The channel 702 is arced along its length. The illustrated embodiment includes two of the channels 702 coupled through one or more members 706. In other embodiments, the carrier includes more or less channels and may be otherwise shaped. Connectors 708 and 710 are affixed to opposing end regions of the channel 702. The illustrated connectors 708 and 710 have closed contours with material free regions extending through along the length of the channel 702.

The connectors 708 and 710 respectively are "female" and "male" type complementary connectors. This allows for coupling the two or more carriers 700, for example, to form a ring of carriers 700. When connected together, the male/female connectors 708 and 710 partially overlap. The carrier 700 and connectors 708 and 710 can be formed from various insulation materials such as a polymer material. The material may also have a relatively high coefficient of thermal expansion. The thickness of the carrier 700 can be controlled through milling, injection molding, or the like.

Figure 8:
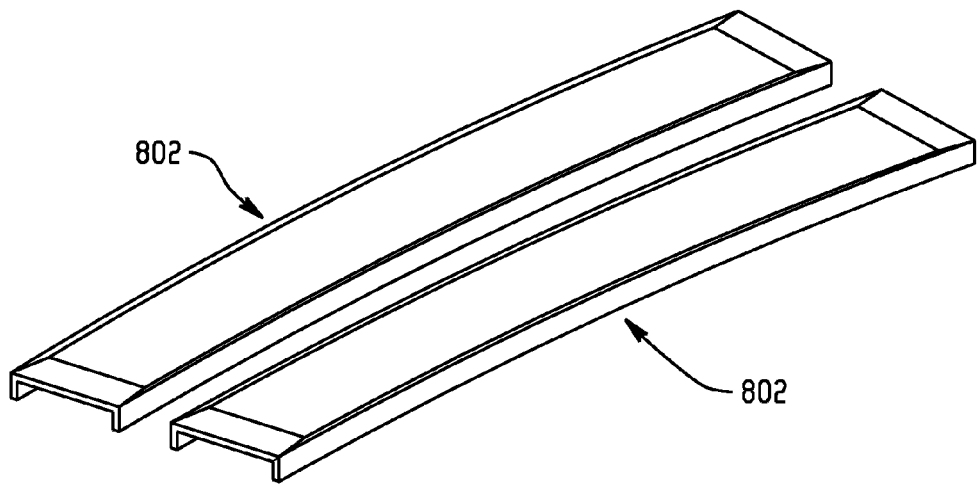
Figure 9:
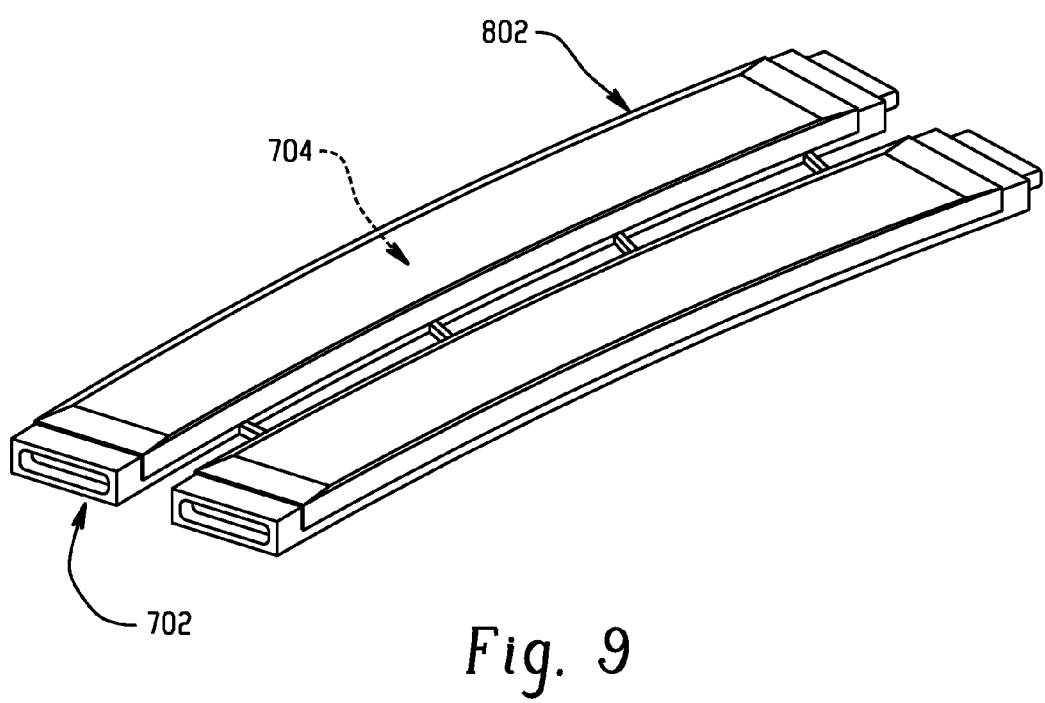
Figure 10:
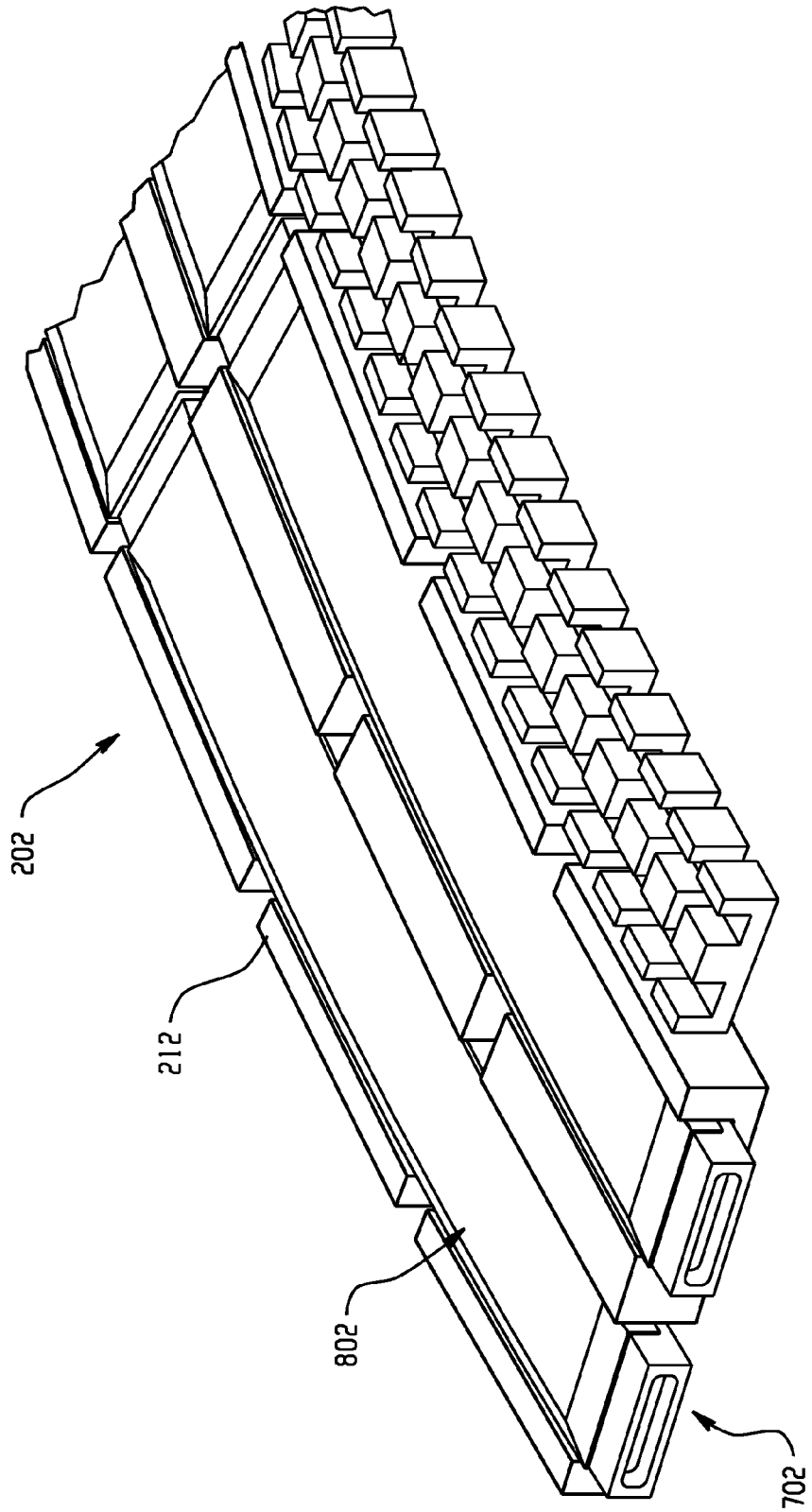
FIG. 10 illustrates the carrier installed in a core of the transformer.

Turning to FIGS. 8 and 9, a complementary cover 802 is also arced and U-shaped. The cover 802 covers the opening 704 (FIG. 7) of the carrier 700. FIG. 10 illustrates the carrier 700 and cover 802 installed in the core 212 (or 216) of the transformer 202. The spacing between the carrier 700 and the cover 802 allows for thermal expansion of the windings, the carrier 700 and/or the cover 802. The cover 802 may snap on or otherwise coupled to the carrier 700.

Figure 11:
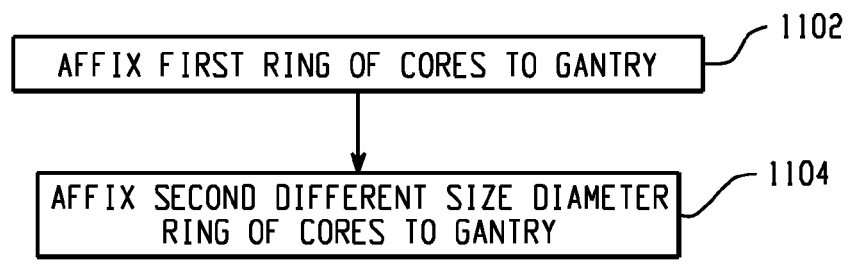
FIG. 11 illustrates an example method.
Figure 12:
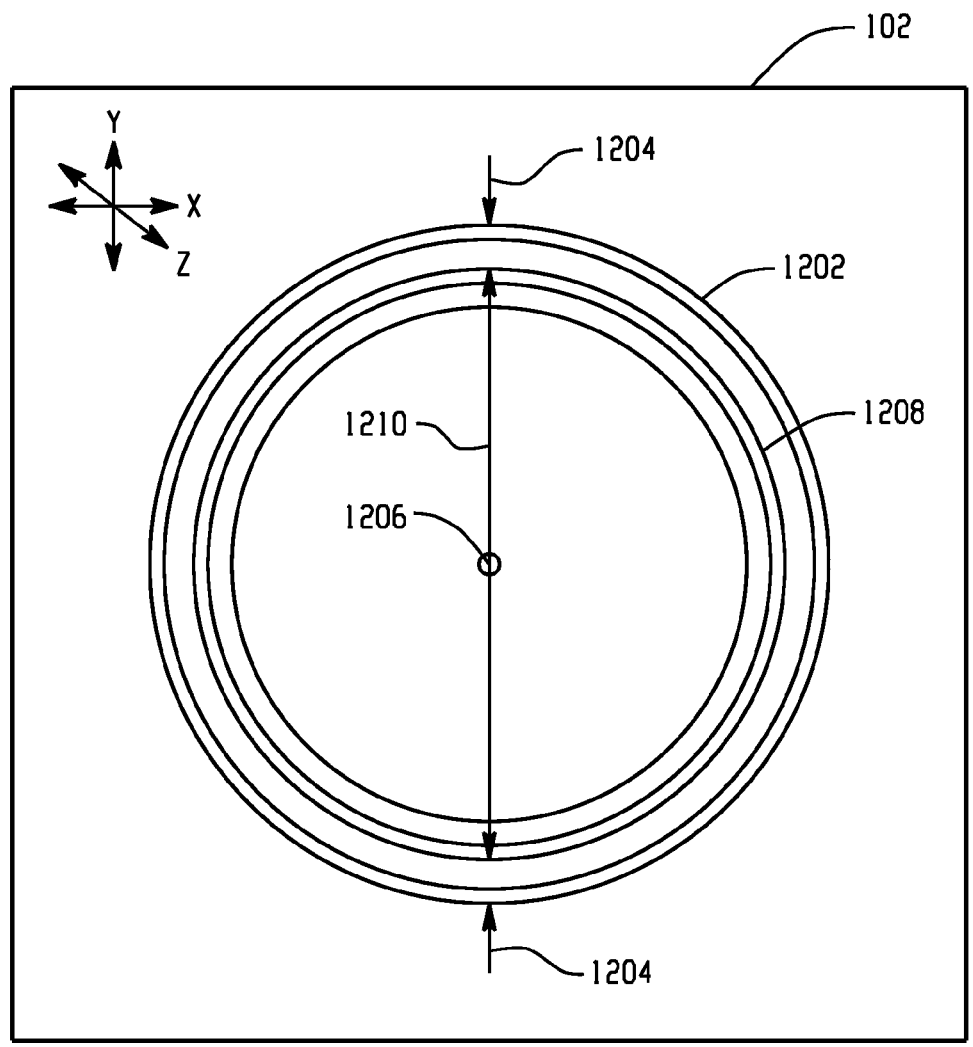
FIG. 12 illustrates an example of concentric rings of cores.

FIG. 11 illustrates a method for affixing the power chain 118 to the system 100, and FIG. 12 illustrates an example of the power chain 118 affixed to the system 100. The method is described in the context of affixing the power chain 118 to the stationary gantry 102. However, the method also applies to affixing the power chain 118 to the rotating gantry 104. At 1102, a first ring of ferromagnetic cores 1202 having a first outer diameter 1204 with respect to an axis of rotation 1206 is affixed to the stationary gantry 102. At 1104, a second ring of ferromagnetic cores 1208 having a second different outer diameter 1210 is affixed to the stationary gantry 102. The first and second rings 1202 and 1208 form concentric rings of ferromagnetic cores about the axis of rotation 1206. Windings may be pre-installed in the cores using a resin or the like. Alternatively, the windings may be installed in the ferromagnetic cores using the carrier 700 (FIG. 7), as described herein. Complementary cores are affixed to the rotating gantry 104. The rings on the stationary and rotating gantries 102 and 104 together form transformers of the power chain 118, which, as described herein, are used to transfer power from the stationary gantry 102 to the rotating gantry 104.

Figure 13:
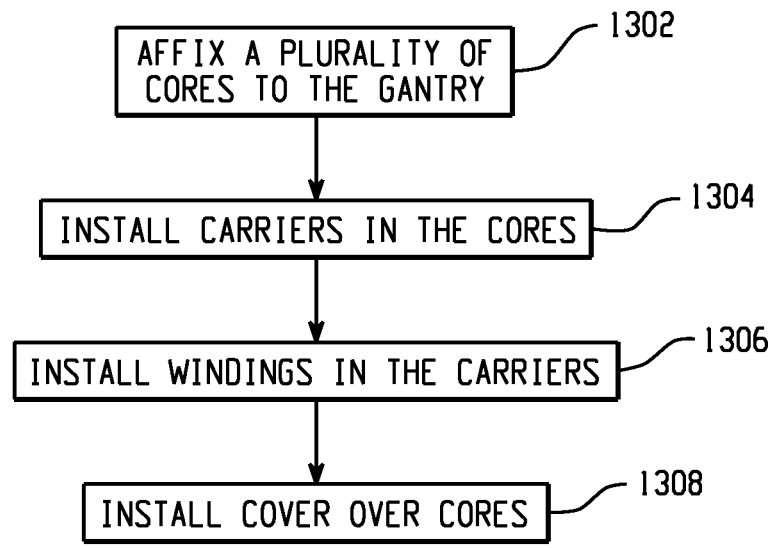
FIG. 13 illustrates an example method.

FIG. 13 illustrates a method for affixing the power chain 118 to the system 100 and is described in the context of affixing the power chain 118 to the stationary gantry 102. Likewise, this method also applies to affixing the power chain 118 to the rotating gantry 104. At 1302 a plurality of ferromagnetic cores are affixed to the stationary gantry 102 to form a ring of cores. The cores are rigidly affixed to the stationary gantry 102 through a fastener such as an adhesive like a glue or other fastener. At 1304, the carriers 700 are installed in the rings of cores. At 1306, the windings are installed in the carriers 700. This can be achieved by lacing the windings through the connectors 708 and 710. The windings can be partly or fully secured in the carrier 700 through an adhesive such as a glue or other adhesive. At 1308, the covers 802 are installed, securing the windings in the carriers 700 with a predetermined alignment.

Figure 14:
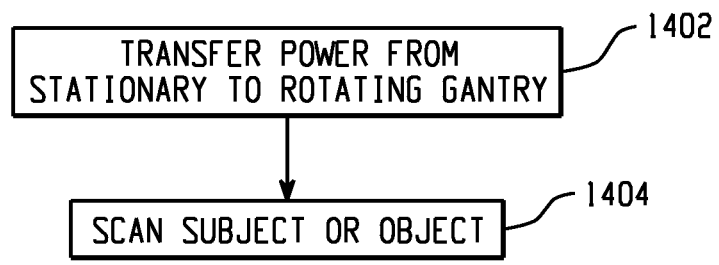
FIG. 14 illustrates an example method.

FIG. 14 illustrates a method. At 1402, power is transferred from the stationary gantry 102 to the rotating gantry 104 via the contactless power chain 118. The power is used to supply power to one or more components supported by the rotating gantry 104. As described herein, in one embodiment the contactless power chain 118 includes at least two transformers that are shifted with respect to each other along the z-axis 108, which may reduce flux coupling therebetween. Additionally or alternatively, the windings of the transformers 202, 204, 306, . . . can be supported and insulted through the insulator 220, 236, which may be a resin, the carrier 700 or other support. At 1404, an object or subject in the examination region 106 of the imaging system 100 is scanned.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
    a stationary gantry;
    a rotating gantry that rotates about a longitudinal axis, the rotating gantry, including:
        a first component supplied with first power; and
        a second component supplied with second power, wherein the first and second power are different; and
    a contactless power chain, including:
        a first transformer for transferring the first power from the stationary gantry to the rotating gantry; and
        a second transformer for transferring the second power from the stationary gantry to the rotating gantry, wherein the first and second transformers are radially offset from each other along a transverse axis and wherein the first and second transformers are shifted relative to each other along the longitudinal axis by a pre-determined finite non-zero distance.

2. The imaging system of claim 1, wherein the first and second transformers are arranged on the stationary and rotating gantries as concentric rings having different diameters about an axis of rotation.

3. The imaging system of claim 1, wherein one of the first or second transformers is rotated along the longitudinal axis with respect to the other one of the first or second transformers.

4. The imaging system of claim 1, wherein the first and second transformers have substantially similar heights and the pre-determined finite non-zero distance is equal to about half of the height.

5. The imaging system of claim 1,
    the first transformer, including:
        a first primary side, with first primary windings, affixed to the stationary gantry; and
        a first secondary side, with first secondary windings, affixed to the rotating gantry,
        wherein the first primary and secondary sides are separated by a gap having a finite non-zero width; and
    the second transformer, including:
        a second primary side, with second primary windings, affixed to the stationary gantry; and
        a second secondary side, with second secondary windings, affixed to the rotating gantry,
        wherein the second primary and secondary sides are separated by a gap having the finite non-zero width.

6. The imaging system of claim 5, wherein at least one of the second primary side or the first secondary side is affixed to the stationary gantry respectively in alignment with a portion of the finite non-zero gaps of the other one of the transformers.

7. The imaging system of claim 6, wherein the alignment substantially minimizes flux coupling between the transformers.

8. The imaging system of claim 4, wherein the transformers are shifted from each other such that leakage flux from one or both of the gaps traverses substantially cores of the other transformer.

9. The imaging system of claim 1, further comprising: a filter of one of the transformers that filters leakage flux from the other one of the transformers.

10. The imaging system of claim 1, wherein first component includes a radiation source.

11. The imaging system of claim 1, the transformers, further comprising: windings and an insulator, wherein the insulator supports the windings in a pre-determined alignment.

12. The imaging system of claim 11, wherein the insulator includes a carrier that inserts into the transformer.

13. The imaging system of claim 1, wherein windings of the contactless power chain are carried by a polymer based carrier.

14. The imaging system of claim 13, the polymer based carrier, comprising:
a channel; and
a cover.

15. The imaging system of claim 14, the channel, comprising:
a U-shaped insulated channel with an open side, wherein the cover covers the open side, thereby insulating the windings therebetween.

16. The imaging system of claim 14, the channel, comprising:
a U-shaped insulated channel with an open side, wherein the cover covers the open side, thereby at least one of aligning or fixing the windings.

17. The imaging system of claim 15, the channel, further comprising: first and second connectors connected to opposing ends of the channel, wherein at least two insulated carriers are connected together through the connectors.

18. The imaging system of claim 13, the contactless power chain, further comprising: a core, wherein the polymer based carrier is carried by the core.

19. The imaging system of claim 13, wherein the cover removably affixes to the polymer based carrier.

20. The imaging system of claim 13, wherein the
first transformer transfers first power from the stationary gantry to the rotating gantry and
a second transformer that transfers second power from the stationary gantry to the rotating gantry.

21. The imaging system of claim 20, wherein the first and second transformers are arranged on the stationary and rotating gantries as concentric rings having different diameters about an axis of rotation.

22. A method, comprising:
transferring, with a first transformer of a contactless power chain, first power from a stationary gantry to a rotating gantry that rotates about a longitudinal axis, wherein the first power is supplied to a first component; and transferring, with a second transformer of the contactless power chain, second power from the stationary gantry to the rotating gantry, wherein the second power is supplied to a second component, wherein the first and second power are different components; wherein the first and second transformers are radially offset from each other along a transverse axis and wherein the first and second transformers are shifted relative to each other along the longitudinal axis by a pre-determined finite non-zero distance.

23. The method of claim 22, wherein the first and second transformers are arranged on the stationary and rotating gantries as concentric rings having different diameters about an axis of rotation.

24. The method of claim 22, wherein the shift is based on a location of a gap between primary and second cores of one of the transformers.

25. The method of claim 22, wherein the transformer includes windings supported by a polymer based carrier.

26. The method of claim 25, the polymer based carrier, comprising:
an insulated channel; and
an insulated channel cover that removeably affixed to the insulated channel.

27. The method of claim 25, wherein the polymer based carrier is carried by a core of the transformers.

28. The method of claim 25, further comprising: pre-aligning the windings in concentric grooves of the carrier.

29. The method of claim 28 further comprising: pre-aligning the windings in the carrier through an adhesive.

* * * * *